United States Patent [19]
Patt et al.

[11] Patent Number: 6,017,951
[45] Date of Patent: Jan. 25, 2000

[54] BUTENOLIDE ENDOTHELIN ANTAGONISTS

[75] Inventors: William C. Patt, Chelsea; Bill R. Reisdorph; Joseph T. Repine, both of Ann Arbor, all of Mich.

[73] Assignee: Warner-Lambert Company, Morris Plains, N.J.

[21] Appl. No.: 09/247,534

[22] Filed: Feb. 10, 1999

Related U.S. Application Data

[62] Division of application No. 08/981,059, filed as application No. PCT/US96/10651, Jun. 21, 1996
[60] Provisional application No. 60/000,904, Jul. 6, 1995.

[51] Int. Cl.[7] ........................ A61K 31/335; C07D 307/32
[52] U.S. Cl. ............................................. 514/464; 549/318
[58] Field of Search ................................... 514/464, 473; 549/318

[56] References Cited

U.S. PATENT DOCUMENTS

| | | | |
|---|---|---|---|
| 4,594,443 | 6/1986 | Bianchi et al. | 560/53 |
| 4,968,817 | 11/1990 | Brima | 549/295 |

FOREIGN PATENT DOCUMENTS

| | | |
|---|---|---|
| 0010347 | 4/1980 | European Pat. Off. . |
| 0099692 | 2/1984 | European Pat. Off. . |
| 0134179 | 3/1985 | European Pat. Off. . |
| 0403891 | 12/1990 | European Pat. Off. . |
| 0436189 | 7/1991 | European Pat. Off. . |
| 5178706 | 7/1993 | Japan . |
| 9116055 | 10/1991 | WIPO . |
| 9219610 | 11/1992 | WIPO . |
| 9505376 | 2/1995 | WIPO . |
| 9623773 | 8/1996 | WIPO . |

OTHER PUBLICATIONS

Stein et al., "The Discovery of Sulfonamide Endothelin Antagonists and the Development of the Orally Active $ET_A$ Antagonist 5–(Dimethylamino)–N–(3, 4–dimethyl–5–isoxazolyl)–1–napthalenesulfonamide", *J. Med. Chem.*, 1994, 37:3, 329–331.

Foley et al., "Reversal of Subarachnoid Hemorrhage–induced Vasoconstriction with an Endothelin Receptor Antagonist", *Neurosurgery*, 1994, 34:1, 108–113.

Rio and Hardy, "Triphényl–3,4,5 H–5 furannone–2, acide cis–benzoyl–3 diphényl–2,3 acrylique et dérivés", *Bulletin de la Société Chimique de France*, 1970, 10, 3572–3578.

Patwardhan and Bagawant, "Claisen–Stobbe Reaction of Phenylacetic Esters & Diketones", *Indian Journal of Chemistry*, 1973, 11:9, 1333–1334.

McEvoy and Allen, "6–(Substituted phenyl)–5–substituted–4,5–dihydro–3(2H)–pyridaziones. Antihypertensive Agents", *J. Med. Chem.*, 1974, 17:3, 281–286.

Dikshit et al., "Synthesis and biological activity of 2,3– and 3,4–diarylfurans and 2,3,4–triaryl–2,5–dihydrofurans", *Indian Journal of Chemistry*, 1990, 29B, 954–960.

Krapf et al., "Thermische Umwandlung der labilen 1:1–Addukte aus Diphenylcyclopropenon bzw. Diphenylcyclopropenthion und Ketenacetalen", *Chem. Ber.*, 1976, 109, 576–596.

Schmand et al., "Synthese eines 1,5–Naphthochinons; zur Struktur des Naphthazarins und zur Stabilität von Chinonen", *Liebigs Ann. Chem.*, 1976, 1560–1576.

Rohrscheidt and Fritz, "Zum Mechanismus der Aminabspaltung bei der Bildung von Pyrrolinonen aus N'–(1–Alkenyl)hydraziden and durch Brunnersche Oxindolsynthese", *Liebigs Ann. Chem.*, 1878, 680–693.

Padwa et al., "Migratory Aptitude Studies in the Photochemical Rearrangement of 2(5H)–Furanones", *J. Am. Chem. Soc.*, 1978, 100:26, 8247–8259.

Chelain et al., "Reaction of Aminocarbene Complexes of Chromium with Alkynes. 1. Formation and Rearrangement of Ketene and Nitrogen Ylide Complexes", *J. Am. Chem. Soc.*, 1992, 114, 8088–8098.

Weinberg and Miller, "Decomposition of 5–Aryl–5–(tert–butylperoxy)–3, 4–diphenyl–2(5H)–furanones", *J. Org. Chem.*, 1979, 44:25, 4722–4725.

Daroca et al., "Reactivity of Pyrrole Pigments. Part 5: Electrophilic Substitution—Nitration and Bromination—of Some Pyrromethenones and 5–Arylmethylene–3, 4–dimethyl–3–pyrrolin–2–ones", *Montaschefte f r Chemie*, 1984, 115, 357–373.

Falsone and Wingen, "Synthese von 2–Oxo–5H–furanen unter Wittig–Horner Bedingungen", *Arch. Pharm.*, 1984, 317, 802–806.

Verma et al., "Smooth Conversion of 3,4–Diarylcoumarins and 3,4,5–Triaryl–2(5H)–furanones to 2H–Chromene and 2,5–Dihydrofuran Derivatives with Dimethyl Sulfide–Borane Complex", *Synthesis*, 1988, 1, 68–70.

Pratapan et al., "Substituent Effects in the Photochemistry of 5–Aryl–3,3–diphenyl–2(3H)–furanones. Steady–State and Laser Flash Photolysis Studies", *J. Org. Chem.*, 1988, 53, 5826–5831.

Krafft and Pankowski, "Butenolide synthesis using acyl cobalt complexes", *Tetrahedron Letters*, 1990, 31:36, 5139–5142.

(List continued on next page.)

*Primary Examiner*—John Kight
*Assistant Examiner*—Charanjit S. Aulakh
*Attorney, Agent, or Firm*—Elizabeth M. Anderson

[57] ABSTRACT

Novel nonpeptides characterized as having a carbamic group which are antagonists of endothelin I are described, as well as methods for their preparation and pharmaceutical compositions containing the same. The compounds are useful in treating elevated levels of endothelin and are therefore useful in the treatment of hypertension, myocardial infarction, diabetes, cerebral vasospasm, cirrhosis, septic shock, congestive heart failure, endotoxic shock, subarachnoid hemorrhage, arrhythminas, asthma, chronic and acute renal failure, preeclampsia, atherosclerotic disorders including Raynaud's disease and restenosis, angina, cancer, pulmonary hypertension, ischemic disease, gastric mucosal damage, hemorrhagic shock, stroke, head injury, and ischemic bowel syndrome.

2 Claims, No Drawings

OTHER PUBLICATIONS

Alcaide and Rodriguez–López, "Reaction of N–Trimethylsilyl Benzil Monoimine with Simple Lithium Ester Enolates. A Synthetic Tool for the Regioselective One–Pot Preparation of Novel Polyfunctional Pyrrolines", *J. Chem. Soc.–Perkin Trans.*, 1990, 1, 2451–2457.

Dinulescu et al., "IX. Reaction of 1–chloro–1, 2–diphenyl–3–aryl–Ξ–allylpalladium complexes with carbon monoxide", *Journal of Organometallic Chemistry*, 1977, 140, 91–96.

Chan et al., "Solvent, chelation and concentration effects on the benzannulation reaction of chromium carbene complexes and acetylenes", *Journal of Organometallic Chemistry*, 1987, 334, 9–56.

Pennanen, "Studies on the furan series. Part VIII. The reaction of ynamines with acyloins. A convenient preparation of 4,5–di(2–furyl and 2–thienyl)–2(5H)–furanones and – furans", *Heterocycles*, 1977, 6:6, 701–706.

Endo and Shudo, "Anionic hetero[3,3]rearrangements. N–Acyl–N'–enylhydrazines to pyrrolidinones", *Heterocycles*, 1992, 33:1, 91–95.

Dötz et al., "LVII. Amidinocarben–Chelatkomplexe des Chroms und Molybdäns: Synthese, Struktur und Cycloadditionen mit Alkinen", *Journal of Organometallic Chemistry*, 1993, 459, 169–176.

Herndon and Zora, "Reaction of Cyclopropylcarbene–Molybdenum Complexes with Alkynes: Formation of Cycloheptadienones under Mild Conditions", *Synlett*, 1993, 5, 363–364.

Tyvorskii and Kukharev, "Reaction of alkyl– and phenyl–substituted 5–aminomethyl–2(5H)–furanones with dimethylamine", *Russian Journal of Organic Chemistry*, 1993, 29:5(2), 840–843.

Clozel et al., "Pathophysiological role of endothelin revealed by the first orally active endothelin receptor antagonist", *Nature*, 1993, 365, 759–761.

Ohno, "Effects of Endothelin–specific Antibodies and Endothelin in Spontaneously Hypertensive Rats", *J. Tokyo Women's Medical College*, 1991, 61:10–11, 951–959.

Lerman et al., "Endothelin Has Biological Actions at Pathophysiological Concentrations", *Circulation*, 1991, 83:5, 1808–1814.

Rodeheffer et al., "Circulating plasma endothelin correlates with the severity of congestive heart failure in humans", *Am. J. Hypertension*, 1991, 4:9A–10A.

Arai et al., "Cloning and expression of a cDNA encoding an endothelin receptor", *Nature*, 1990, 348, 730–732.

Sakurai et al., "Cloning of a cDNA encoding a non–isopeptide–selective subtype of the endothelin receptor", *Nature*, 1990, 348, 732–735.

Lin et al., "Cloning and functional expression of a vascular smooth muscle endothelin 1 receptor", *Proc. Natl. Acad. Sci. USA*, 1991, 88, 3185–3189.

Sakamoto et al., "Cloning and functional expression of human cDNA for the $ET_B$ endothelin receptor", *Biochem. Biophys. Res. Chem.*, 1991, 178:2, 656–663.

Hosoda et al., "Cloning and expression of human endothelin–1 receptor cDNA", *FEBS Lett.*, 1991, 287:1,2; 23–26.

Takayanagi et al., "Presence of non–selective type of endothelin receptor on vascular endothelium and its linkage to vasodilation", *FEBS Lett.*, 1991, 282:1, 103–106.

Panek et al., "Endothelin and structurally related analogs distinguish between endothelin receptor subtypes", *Biochem. Biophys. Res. Chem.*, 1992, 183:2, 566–571.

Saeki et al., "[$Ala^{1,3,11,15}$]Endothelin–1 analogs with $Et_B$ agonistic activity", *Biochem. Biophys. Res. Chem.*, 1991, 179:1, 286–292.

Nakagawa et al., "Measurement of Immunoreactive Endothelin–1 in Plasma of a Patient with Malignant Hemangioendothelioma", *Nippon Hifuka Gakkai Zasshi*, 1990, 100, 1453–1456.

Noguchi et al., "An Endothelin $(ET)_A$ Receptor Antagonists, BQ–123, Blocks ET–1 Induced Bronchoconstriction and Tracheal Smooth Muscle (TSM) Contraction in Allergic Sheep", *Am. Rev. Respir. Dis.*, 1992, 145 (4 Part 2), A858.

Clark et al., "Plasma endothelin levels in preeclampsia: Elevation and correlation with uric acid levels and renal impairment", *Am. J. Obstet Gynecol.*, 1992, 166:3, 962–968.

Pittet et al., "Elevated Plasma Endothelin–1 Concentrations Are Associated with the Severity of Illness in Patients with Sepsis", *Ann. Surg.*, 1991, 213:3, 261–264.

Gandhi et al., "Endothelin, a Potent Peptide Agonist in the Liver", *J. Biol. Chem.*, 1990, 265:29, 17432–17435.

Kanno et al., "Endothelin–1 and Vasculitis", *J. Amer. Med. Assoc.*, 1990, 264:22, 2868.

Zamora et al., "Serum endothelin–1 concentrations and cold provocation in primary Raynaud's phenomenon", *Lancet*, 1990, 336, 1144–1147.

Tahara et al., "Circulating Immunoreactive Endothelin in Patients Undergoing Percutaneous Transluminal Coronary Angioplasty", *Metabolism*, 1991, 40:12, 1235–1237.

Stewart et al., "Increased Plasma Endothelin–1 in Pulmonary Hypertension: Marker or Mediator of Disease?", *Annals of Internal Medicine*, 1991, 114:6, 464–469.

Yasuda et al., "Circulating immunoreactive endothelin in ischemic heart disease", *American Heart Journal*, 1990, 119:4, 801–806.

Stewart et al., "Plasma endothelin in coronary venous blood from patients with either stable or unstable angina", *Br. Heart J.*, 1991, 66, 7–9.

López–Farré et al., "A role for endothelin in the maintenance of post–ischaemic renal failure in the rat", *Journal of Physiology*, 1991, 444, 513–522.

Stockenhuber et al., "Plasma levels of endothelin in chronic renal failure and after renal transplantation: impact on hypertension and cyclosporin A–associated nephrotoxicity", *Clonical Science*, 1992, 82, 255–258.

Miura et al., "Ischemic Bowel Necrosis Induced by Endothelin–1: An Experimental Model in Rats", *Digestion*, 1991, 48, 163–172.

Masuda et al., "Effect of intravascular ethanol on modulation of gastric mucosal integrity: possible role of endothelin–1", *Am. J. Physiol.*, 1992, 262, G785–G790.

Murch et al., "High endothelin–1 immunoreactivity on Crohn's disease and ulcerative colitis", *Lancet*, 1992, 339, 381–384.

Clozel and Watanabe, "BQ–123, A Peptidic Endothelin $ET_A$ Receptor Antagonist, Prevents the Early Cerebral Vasospasm Following Subarachnoid Hemorrhage After Intracisternal but not Intravenous Injection", *Life Sciences*, 1993, 52:9, 825–834.

Basil et al., "Hemodynamic effects of an endothelin (ET) receptor antagonist in three rat models of hypertension", *J. Hypertension*, 1992, 10(Suppl 4), S49.

Han et al., "Cardiac and vascular actions of sarafotoxin S6b and endothelin–1", *Life Sciences*, 1990, 46:11, 767–775.

Allen and Frame, "The condensation of certain –ketonic esters with aromatic aldehydes", *Can. J. Research*, 1932, 6, 605–613.

Allen et al., "The condensation of certain -ketonic esters with aromatic aldehydes. II", *Can. J. Research*, 1933, 8, 137–141.

Canévet and Graff, "Rëeactions de Friedel–Crafts de dérivés aromatiques sur des composés dicarbonylés–1,4 éthyléniques–2,3.II Alkylations par quelques hydroxy–5 ou chloro–5 hydro–2,5 furannones–2. Nouvelle méthode de synthèse des acids 1H–indènecarboxyliques–1", *Tetrahedron*, 1978, 34, 1935–1942.

Mise et al., "Rhodium Carbonyl Catalyzed Carbonylation of Unsaturated Compounds. 2. Synthesis of 5–Alkoxy–2(5H)–furanones by the Carbonylation of Acetylenes in Alcohol", *J. Org. Chem.*, 1983, 48, 238–242.

Anselmi et al., "A One–Step Conversion of N–Acylaminoketones into 5–Alkylidene–3–pyrrolin–2–ones", *J. Heterocyclic Chem.*, 1983, 20, 687–689.

Yoshida et al., "Cycloaddition of Diphenylcyclopropenone with Carboximidate, Carboximidamide, and Carboximidothioate", *Bull. Chem. Soc. Jpn.*, 1983, 56, 3849–3850.

Watanabe et al., "Endothelin in myocardial infarction", *Nature*, 1990, 344, 114.

Margulies et al., "Increased Endothelin in Experimental Heart Failure", *Circulation*, 1990, 82:6, 2226–2230.

Kon et al., "Glomerular Actions of Endothelin In Vivo", *J. Clin. Invest.*, 1989, 83, 1762–1767.

Perico et al., "Endothelin Mediates the Renal Vasoconstriction Induced by Cyclosporine in the Rat", *J. Am. Soc. Nephrol.*, 1990, 1:1, 76–83.

Koshi et al., "Inhibition of Endothelin (ET)–1– and ET–2–Induced Vasoconstriction by Anti–ET–1 Monoclonal Antibody", *Chem. Pharm. Bull.*, 1991, 39:5, 1295–1297.

Miyamori et al., "Systemic and regional effects of endothelin in rabbits: effects of endothelin antibody", *Clin. Exp. Pharmacol. Physiol.*, 1990, 17, 691–696.

Collier et al., "Plasma Endothelinlike Immunoreactivity Levels in IDDM Patients With Microalbuminuria", *Diabetes Care*, 1992, 15:8, 1038–1040.

Nikolov and Semkova, "Cerebrovascular and CNS Effects of Endothelins—Target for Pharmacological Modification?", *Drugs of Today*, 1992, 28:5, 303–310.

Lerman et al., "Circulating and tissue endothelin immunoreactivity in advanced atherosclerosis", *New England J. Med.*, 1991, 325:14, 997–1001.

Rovero et al., "Structure–activity studies on endothelin (16–21), the C–terminal hexapeptide of the endothelins, in the guinea–pig bronchus", *Br. J. Pharmacol.*, 1990, 101, 232–234.

Clozel et al., "The discovery of Ro 46–2005, an orally available non–peptide antagonist of $ET_A$ and $ET_B$ receptors", *Third Intl. Conf. on Endothelin*, Abstract Book, Feb. 5–17, 1993, p. 17.

Doherty et al., "Design of C–terminal peptide antagonists of endothelin: structure–activity relationships of ET–1[16–21, D–His$^{16}$]", *Bioorg. & Med. Chem. Lett.*, 1990, 3:4, 497–502.

Allen et al., "Certain reactions of gamma ketonic Acids", *Can. J. Research*, 1934, 11, 382–394.

Allen et al., "–Arayl– –aroylpropionic acids and their condensation products with aromatic aldehydes", *Can. J. Chem.*, 1956, 34, 926–930.

PCT International Search Report, PCT/US96/10651.

BUTENOLIDE ENDOTHELIN ANTAGONISTS

This application is a Div. of Ser. No. 08/981,059 filed Dec. 15, 1997 which is a 371 of PCT/US96/10651 filed Jun. 21, 1996 and claims priority of provisional application No. 60/000,904 filed Jul. 6, 1995

BACKGROUND OF THE INVENTION

The present invention relates to novel antagonists of endothelin useful as pharmaceutical agents, to methods for their production, to pharmaceutical compositions which include these compounds and a pharmaceutically acceptable carrier, and to pharmaceutical methods of treatment. More particularly, the compounds of the present invention are antagonists of endothelin useful in treating elevated levels of endothelin, acute and chronic renal failure, hypertension, myocardial infarction and myocardial ischemia, cerebral vasospasm, cirrhosis, septic shock, congestive heart failure, endotoxic shock, subarachnoid hemorrhage, arrhythmias, asthma, preeclampsia, atherosclerotic disorders including Raynaud's disease and restenosis, angina, cancer, pulmonary hypertension, ischemic disease, gastric mucosal damage, hemorrhagic shock, ischemic bowel disease, and diabetes.

Also, the compounds will be useful in cerebral ischemia or cerebral infarction resulting from a range of conditions such as thromboembolic or hemorrhagic stroke, cerebral vasospasm, head injury, hypoglycemia, cardiac arrest, status epilepticus, perinatal asphyxia, anoxia such as from drowning, pulmonary surgery, and cerebral trauma.

Endothelin is involved in many human disease states.

Several studies have been reported with both peptide and nonpeptide ET antagonists showing efficacy in various models of subarachnoid hemorrhage (SAH). For example, BQ-123-prevents early cerebral vasospasm following SAH in various rat (Clozel M., et al., *Life Sci.*, 1993;52:825) and rabbit (Lee K. S., et al., *Cerebral Vasospasm*, 1993:217; and *Neurosurgery*, 1994; 34:108) models. FR 139317 significantly inhibited the vasoconstriction of the basilar artery after 7 days in a canine two-hemorrhage model of SAH (Nirei H., et al., *Life Sci.*, 1993;52:1869). BQ-485 also significantly inhibited the vasoconstriction of the basilar artery after 7 days in a canine two-hemorrhage model of SAH (Yano, et al., *Biochem Biophys. Res Commun.*, 1993; 195:969). Ro 46-2005 (Clozel M., et al., *Nature*, 1993;365:759) has been shown to prevent early cerebral vasospasm following SAH in the rat with no significant effect on systemic arterial blood pressure. Treatment with Ro 47-0203=Bosentan (Clozel, et al., *Circulation*, 1993;88(4) part 2:0907) to rabbits with SAH had a 36±7% reduction of basilar artery cross-sectional area compared to sham rabbits. All of these studies show in vivo efficacy of endothelin antagonists in cerebral vasospasm resulting from SAH.

Endothelin-1 (ET-1), a potent vasoconstrictor, is a 21 amino acid bicyclic peptide that was first isolated from cultured porcine aortic endothelial cells. Endothelin-1, is one of a family of structurally similar bicyclic peptides which include; ET-2, ET-3, vasoactive intestinal contractor (VIC), and the sarafotoxins (SRTXs).

Several in vivo studies with ET antibodies have been reported in disease models. Left coronary artery ligation and reperfusion to induce myocardial infarction in the rat heart, caused a 4- to 7-fold increase in endogenous endothelin levels. Administration of ET antibody was reported to reduce the size of the infarction in a dose-dependent manner (Watanabe T., et al., "Endothelin in Myocardial Infarction," *Nature*, (Lond.) 1990;344:114). Thus, ET may be involved in the pathogenesis of congestive heart failure and myocardial ischemia (Margulies K. B., et al., "Increased Endothelin in Experimental Heart Failure," *Circulation*, 1990;82:2226).

Studies by Kon and colleagues using anti-ET antibodies in an ischemic kidney model, to deactivate endogenous ET, indicated the peptide's involvement in acute renal ischemic injury (Kon V., et al., "Glomerular Actions of Endothelin In Vivo," *J. Clin. Invest.*, 1989;83:1762). In isolated kidneys, preexposed to specific antiendothelin antibody and then challenged with cyclosporine, the renal perfusate flow and glomerular filtration rate increased, while renal resistance decreased as compared with isolated kidneys preexposed to a nonimmunized rabbit serum. The effectiveness and specificity of the anti-ET antibody were confirmed by its capacity to prevent renal deterioration caused by a single bolus dose (150 pmol) of synthetic ET, but not by infusion of angiotensin II, norepinephrine, or the thromboxane $A_2$ mimetic U-46619 in isolated kidneys (Perico N., et al., "Endothelin Mediates the Renal Vasoconstriction Induced by Cyclosporine in the Rat," *J. Am. Soc. Nephrol.*, 1990;1:76).

Others have reported inhibition of ET-1 or ET-2-induced vasoconstriction in rat isolated thoracic aorta using a monoclonal antibody to ET-1 (Koshi T., et al., "Inhibition of Endothelin (ET)-1 and ET-2-Induced Vasoconstriction by Anti-ET-1 Monoclonal Antibody," *Chem. Pharm. Bull.*, 1991;39:1295).

Combined administration of ET-1 and ET-1 antibody to rabbits showed significant inhibition of the blood pressure (BP) and renal blood flow responses (Miyamori I., et al., Systemic and Regional Effects of Endothelin in Rabbits: Effects of Endothelin Antibody,° *Clin. Exp. Pharmacol. Physiol.*, 1990;17:691).

Other investigators have reported that infusion of ET-specific antibodies into spontaneously hypertensive rats (SHR) decreased mean arterial pressure (MAP), and increased glomerular filtration rate and renal blood flow. In the control study with normotensive Wistar-Kyoto rats (WKY) there were no significant changes in these parameters (Ohno A., Effects of Endothelin-Specific Antibodies and Endothelin in Spontaneously Hypertensive Rats," *J. Tokyo Women's Med. Coll.*, 1991;61:951).

In addition, elevated levels of endothelin have been reported in several disease states (see Table I below).

Burnett and coworkers recently demonstrated that exogenous infusion of ET (2.5 ng/kg/mL) to anesthetized dogs, producing a doubling of the circulating concentration, did have biological actions (Lerman A., et al., "Endothelin has Biological Actions at Pathophysiological Concentrations," *Circulation*, 1991; 83:1808). Thus heart rate and cardiac output decreased in association with increased renal and systemic vascular resistances and antinatriuresis. These studies support a role for endothelin in the regulation of cardiovascular, renal, and endocrine function.

In congestive heart failure in dogs and humans, a significant 2- to 3-fold elevation of circulating ET levels has been reported (Rodeheffer R. J., et al., "Circulating Plasma Endothelin Correlates With the Severity of Congestive Heart Failure in Humans," *Am. J. Hypertension*, 1991;4:9A).

The distribution of the two cloned receptor subtypes, termed $ET_A$ and $ET_B$, have been studied extensively (Arai H., et al., *Nature*, 1990;348:730, Sakurai T., et al., *Nature*, 1990;348:732). The $ET_A$, or vascular smooth muscle receptor, is widely distributed in cardiovascular tissues and in certain regions of the brain (Lin H. Y., et al., *Proc. Natl. Acad. Sci.*, 1991;88:3185). The $ET_B$ receptor, originally cloned from rat lung, has been found in rat cerebellum and in endothelial cells, although it is not known if the $ET_B$ receptors are the same from these sources. The human ET receptor subtypes have been cloned and expressed (Sakamoto A., et al., *Biochem. Biophys. Res. Chem.*, 1991;178:656, Hosoda K., et al., *FEBS Lett.*, 1991;287:23). The $ET_A$ receptor clearly mediates vasoconstriction and there have been a few reports implicating the $ET_B$ receptor in the initial vasodilatory response to ET (Takayanagi R., et al., *FEBS Lett.*, 1991;282:103). However, recent data has shown that the $ET_B$ receptor can also mediate vasoconstriction in some tissue beds (Panek R. L., et al., *Biochem. Biophys. Res. Commun.*, 1992;183(2):566).

A recent study showed that selective $ET_B$ agonists caused only vasodilation in the rat aortic ring, possibly through the release of EDRF from the endothelium (ibid). Thus, reported selective $ET_B$ agonists, for example, the linear analog ET[1, 3,11,15-Ala] and truncated analogs ET[6-21, 1,3,11,15-Ala], ET[8-21,11,15-Ala], and N-Acetyl-ET[10-21,11,15-Ala] caused vasorelaxation in isolated, endothelium-intact porcine pulmonary arteries (Saeki T., et al., *Biochem. Biophys. Res. Commun.*, 1991;179:286). However, some ET analogs are potent vasoconstrictors in the rabbit pulmonary artery, a tissue that appears to possess an $ET_B$, nonselective type of receptor (ibid).

Plasma endothelin-1 levels were dramatically increased in a patient with malignant hemangioendothelioma (Nakagawa K. et al., *Nippon Hifuka Gakkai Zasshi*, 1990;100:1453–1456).

The ET receptor antagonist BQ-123 has been shown to block ET-1 induced bronchoconstriction and tracheal smooth muscle contraction in allergic sheep providing evidence for expected efficacy in bronchopulmonary diseases such as asthma (Noguchi, et al., *Am. Rev. Respir. Dis.*, 1992;145(4 Part 2):A858).

Circulating endothelin levels are elevated in women with preeclampsia and correlate closely with serum uric acid levels and measures of renal dysfunction. These observations indicate a role for ET in renal constriction in preeclampsia (Clark B. A., et al., *Am. J. Obstet. Qynecol.*, 1992;166:962–968).

Plasma immunoreactive endothelin-1 concentrations are elevated in patients with sepsis and correlate with the degree of illness and depression of cardiac output (Pittett J., et al., *Ann Surg.*, 1991;213(3):262).

In addition the ET-1 antagonist BQ-123 has been evaluated in a mouse model of endotoxic shock. This $ET_A$ antagonist significantly increased the survival rate in this model (Toshiaki M., et al., 20.12.90. EP 0 436 189 A1).

Endothelin is a potent agonist in the liver eliciting both sustained vasoconstriction of the hepatic vasculature and a significant increase in hepatic glucose output (Gandhi C. B., et al., *Journal of Biological Chemistry*, 1990;265(29):17432). In addition increased levels of plasma ET-1 have been observed in microalbuminuric insulin-dependent diabetes mellitus patients indicating a role for ET in endocrine disorders such as diabetes (Collier A., et al., *Diabetes Care*, 1992;15(8):1038).

$ET_A$ antagonist receptor blockade has been found to produce an antihypertensive effect in normal to low renin models of hypertension with a time course similar to the inhibition of ET-1 pressor responses (Basil M. K., et al., *J. Hypertension*, 1992;10(Suppl 4): S49). The endothelins have been shown to be arrhythmogenic, and to have positive chronotropic and inotropic effects, thus ET receptor blockade would be expected to be useful in arrhythmia and other cardiovascular disorders (Han S.-P., et al., *Life Sci.*, 1990;46:767).

The widespread localization of the endothelins and their receptors in the central nervous system and cerebrovascular circulation has been described (Nikolov R. K., et al., *Drugs of Today*, 1992;28(5): 303–310). Intracerebroventricular administration of ET-1 in rats has been shown to evoke several behavioral effects. These factors strongly suggest a role for the ETs in neurological disorders. The potent vasoconstrictor action of ETs on isolated cerebral arterioles suggests the importance of these peptides in the regulation of cerebrovascular tone. Increased ET levels have been reported in some CNS disorders, i.e., in the CSF of patients with subarachnoid hemorrhage and in the plasma of women with preeclampsia. Stimulation with ET-3 under conditions of hypoglycemia have been shown to accelerate the development of striatal damage as a result of an influx of extracellular calcium. Circulating or locally produced ET has been suggested to contribute to regulation of brain fluid balance through effects on the choroid plexus and CSF production. ET-1 induced lesion development in a new model of local ischemia in the brain has been described.

Circulating and tissue endothelin immunoreactivity is increased more than twofold in patients with advanced atherosclerosis (Lerman A., et al., *New England J. Med.*, 1991;325:997–1001). Increased endothelin immunoreactivity has also been associated with Buerger's disease (Kanno K., et al., *J. Amer. Med. Assoc.*, 1990;264:2868) and Raynaud's phenomenon (Zamora M.R., et al., *Lancet*, 1990;336:1144–1147).

An increase of circulating endothelin levels was observed in patients that underwent percutaneous transluminal coronary angioplasty (PTCA) (Tahara A., et al., *Metab. Clin. Exp.*, 1991;40:1235–1237).

Increased plasma levels of endothelin have been measured in rats and humans (Stewart D. J., et al., *Ann, Internal Medicine*, 1991;114:464–469) with pulmonary hypertension.

Elevated levels of endothelin have also been measured in patients suffering from ischemic heart disease (Yasuda M., et al., *Amer. Heart J.*, 1990;119:801–806) and either stable or unstable angina (Stewart J.T., et al., *Br. Heart J.*, 1991;66:7–9).

Infusion of an endothelin antibody 1 hour prior to and 1 hour after a 60 minute period of renal ischaemia iresulted in changes in renal function versus control. In addition, an increase in glomerular platelet-activating factor was attributed to endothelin (Lopez-Farre A., et al., *J. Physiology*, 1991;444:513–522). In patients with chronic renal failure as well as in patients on regular hemodialysis treatment mean plasma endothelin levels were significantly increased (Stockenhuber F., et al., *Clin. Sci.* (Lond.), 1992;82:255–258).

Local intra-arterial administration of endothelin has been shown to induce small intestinal mucosal damage in rats in a dose-dependent manner (Mirua S., et al., *Digestion*, 1991;48:163–172). Furthermore, it has been shown that an anti-ET-1 antibody reduced ethanol-induced vasoconstriction in a concentration-dependent manner (Masuda E., et al., *Am. J. Physiol.*, 1992;262:G785–G790). Elevated endothelin levels have been observed in patients suffering from Crohn's disease and ulcerative colitis (Murch S. H., et al., *Lancet*, 1992;339:381–384).

At the 3rd International Conference on Endothelin, Houston, Tex., February 1993, the nonpeptide endothelin antagonist RO 46-2005 has been reported to be effective in models of acute renal ischemia and subarachnoid hemorrhage in rats (Clozel M., et al., "Pathophysiological role of endothelin revealed by the first orally active endothelin receptor antagonist," *Nature*, 1993;365:759). In addition, the $ET_A$ antagonist BQ-123 has been shown to prevent early cerebral vasospasm following subarachnoid hemorrhage (Clozel M. and Watanabe H., *Life sci.*, 1993;52:825–834.

Recently, an $ET_A$ selective antagonist demonstrated an oral antihypertensive effect (Stein P. D., et al., "The Discovery of Sulfonamide Endothelin Antagonists and the Development of the Orally Active $ET_A$ Antagonist 5-(Dimethylamino)-N-(3,4-dimethyl-5-isoxazolyl)-1-naphthalenesulfonamide," *J. Med. Chem.*, 1994;37:329–331.

Table I below summarizes some of the conditions in which ET-1 is involved.

TABLE I

Plasma Concentrations of ET-1 in Humans

| Condition | Normal Control | ET Plasma Levels Reported (pg/mL) |
|---|---|---|
| Atherosclerosis | 1.4 | 3.2 pmol/L |
| Surgical operation | 1.5 | 7.3 |
| Buerger's disease | 1.6 | 4.8 |
| Takayasu's arteritis | 1.6 | 5.3 |
| Cardiogenic shock | 0.3 | 3.7 |
| Congestive heart failure (CHF) | 9.7 | 20.4 |
| Mild CHF | 7.1 | 11.1 |
| Severe CHF | 7.1 | 13.8 |
| Dilated cardiomyopathy | 1.6 | 7.1 |
| Preeclampsia | 10.4 pmol/L | 22.6 pmol/L |
| Pulmonary hypertension | 1.45 | 3.5 |
| Acute myocardial infarction | 1.5 | 3.3 |
| (several reports) | 6.0 | 11.0 |
|  | 0.76 | 4.95 |
|  | 0.50 | 3.8 |
| Subarachnoid hemorrhage | 0.4 | 2.2 |
| Crohn's Disease | 0–24 fmol/mg | 4–64 fmol/mg |
| Cold pressor test | 1.2 | 8.4 |
| Raynaud's phenomenon | 1.7 | 5.3 |
| Raynaud's/hand cooling | 2.8 | 5.0 |
| Hemodialysis | <7 | 10.9 |
| (several reports) | 1.88 | 4.59 |
| Chronic renal failure | 1.88 | 10.1 |
| Acute renal failure | 1.5 | 10.4 |
| Uremia before hemodialysis | 0.96 | 1.49 |
| Uremia after hemodialysis | 0.96 | 2.19 |
| Essential hypertension | 18.5 | 33.9 |
| Sepsis syndrome | 6.1 | 19.9 |
| Postoperative cardiac | 6.1 | 11.9 |
| Inflammatory arthritides | 1.5 | 4.2 |
| Malignant hemangioendothelioma | 4.3 (after removal) | 16.2 |

Copending U.S. application Ser. No. 08/384,083 covers nonpeptide endothelin antagonists of formula

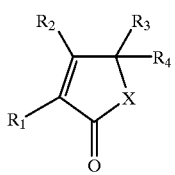

I or a tautomeric open chain keto-acid form thereof or a pharmaceutically acceptable salt thereof wherein $R_1$ is cycloalkyl substituted or unsubstituted of from
   3 to 12 carbon atoms, phenyl substituted with from 1 to 5 substituents, naphthyl unsubstituted or substituted with from
   1 to 5 substituents, or heteroaryl unsubstituted or substituted with from
   1 to 5 substituents;

$R_2$ is alkyl substituted or unsubstituted straight, or branched of from 1 to 12 carbon atoms, cycloalkyl substituted or unsubstituted of from
   3 to 12 carbon atoms, aryl which is unsubstituted or substituted with
   from 1 to 5 substituents, heteroaryl which is unsubstituted or substituted
   with from 1 to 3 substituents;

$R_3$ is alkyl substituted or unsubstituted straight, or branched, of from 1 to 12 carbon atoms, cycloalkyl substituted or unsubstituted of from
   3 to 12 carbon atoms, aryl which is unsubstituted or substituted with
   from 1 to 5 substituents, heteroaryl which is unsubstituted or substituted
   with from 1 to 3 substituents;

$R_4$ is hydroxy or $OR_5$,
   $SR_5$, wherein $R_5$ is alkyl or substituted alkyl of from 1 to 7 carbon atoms, or
   $(CH_2)_nOR_5$ wherein n is an integer of from 1 to 3;

X is O or S;

with the proviso that when $R_1$ is monosubstituted phenyl and the substituent is p-methoxy, $R_3$ is not unsubstituted phenyl, monosubstituted phenyl, or mesityl and with the further proviso when $R_2$ is alkyl substituted, the substituent is not oxygen at the α-position to the furanone ring.

This application for patent is hereby incorporated by reference.

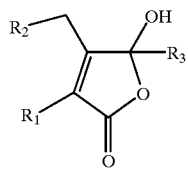

IA wherein:

| $R_1$ | $R_2$ | $R_3$ |
|---|---|---|
| phenyl | phenyl | phenyl |
| phenyl | phenyl | p-chlorophenyl |
| phenyl | phenyl | p-bromophenyl |
| piperonyl 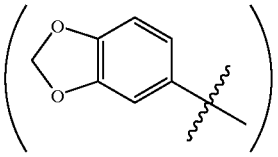 | phenyl | p-chlorophenyl |
| phenyl | o-chlorophenyl | phenyl |
| phenyl | phenyl | p-phenyl-phenyl |
| anisyl (p-methoxyphenyl) | phenyl | phenyl |
| anisyl | α-furyl | phenyl |
| phenyl | piperonyl | p-chlorophenyl |
| anisyl | o-chlorophenyl | phenyl |
| anisyl | o-methoxyphenyl | phenyl |
| phenyl | phenyl | mesityl |
| phenyl | phenyl | p-methylphenyl |
| phenyl | o-chlorophenyl | p-chlorophenyl |
| phenyl | phenyl | p-methoxy-phenyl |
| anisyl | o-methylphenyl | phenyl |
| phenyl | piperonyl | p-bromophenyl |
| phenyl | piperonyl | p-methoxy-phenyl | are all known. However, the methods of using 2(5H)-furanone, 3-(1,3-benzodioxol-5-yl)-5-(4-chlorophenyl)-5-hydroxy-4-(phenylmethyl)- and a pharmaceutical composition containing it are taught in the above co-pending application.

Japanese Patent Application Number 5[1993]178706 covers compounds of formula

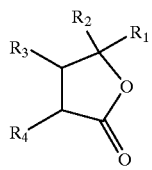

where $R_2$ represents a 1 to 10 carbon alkyl group, 3 to 6 carbon cycloalkyl group, 2 to 10 carbon alkenyl group, 2 to 10 carbon alkynyl group, or phenylalkyl group with a total of less than 10 carbons, $R_2$ represents a hydrogen atom or hydroxyl group, $R_3$ and $R_4$ each represent a lower alkyl group, or $R_3$ and $R_4$ together represent an alkylene group with a total of 3 to 6 carbons. The compounds are disclosed as insect repellents.

SUMMARY OF THE INVENTION

The present invention includes compounds of Formula I

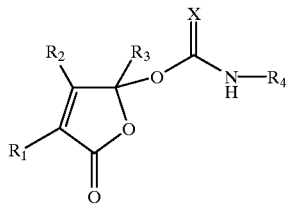

I or a pharmaceutically acceptable salt thereof wherein:
$R_1$ is cycloalkyl substituted or unsubstituted of from
3 to 12 carbon atoms, phenyl substituted with from 1 to
5 substituents, naphthyl unsubstituted or substituted with from
1 to 5 substituents, or heteroaryl unsubstituted or substituted with from
1 to 5 substituents;
$R_2$ is alkyl substituted or unsubstituted straight,
or branched, of from 1 to 12 carbon atoms,
cycloalkyl substituted or unsubstituted of from 3 to 12 carbon atoms,
aryl which is unsubstituted or substituted with from 1 to 5 substituents,
heteroaryl which is unsubstituted or substituted with from 1 to 5 substituents,
$R_3$ is alkyl substituted or unsubstituted straight,
or branched, of from 1 to 12 carbon atoms,
cycloalkyl substituted or unsubstituted of from 3 to 12 carbon atoms,
aryl which is unsubstituted or substituted with from 1 to 5 substituents,
heteroaryl which is unsubstituted or substituted with from 1 to 5 substituents;

$R_4$ is alkyl, substituted or unsubstituted with from 1 to 5 substituents;
aryl unsubstituted or substituted with from 1 to 5 substituents;
heteroaryl unsubstituted or substituted with from 1 to 5 substituents;
X is O or S;

Preferred compounds of the instant invention are those of Formula I wherein
$R_1$ is phenyl substituted with from 1 to 5 substituents, naphthyl unsubstituted or substituted with from 1 to 5 substituents, or heteroaryl unsubstituted or substituted with from 1 to 5 substituents;
$R_2$ is alkyl substituted or unsubstituted straight, or branched, of from 1 to 7 carbon atoms,
$R_3$ is aryl substituted or unsubstituted, heteroaryl substituted or unsubstituted;
$R_4$ is alkyl, unsubstituted or substituted with from 1 to 5 substituents;
aryl unsubstituted or substituted with from 1 to 5 substituents;
heteroaryl unsubstituted or substituted with from 1 to 5 substituents; and
X is O or S.

More preferred compounds of the instant invention are those of Formula I wherein
$R_1$ is 4-piperonyl,
3-methoxyphenyl,
3,5 dimethyl,
3,5-dimethoxyphenyl,

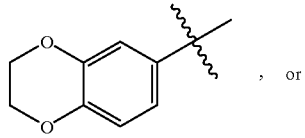

3-methoxy-4,5-methylenedioxyphenyl;
R2 is benzyl,
44-piperonylmethyl,
4-isopropylbenzyl,
1-naphthylmethyl,
2-naphthylmethyl,
3-thiophenylmethyl,
2-thiophenylmethyl,
3,4-dichlorobenzyl,
3(N-Me)indolylmethyl,
3,4-dimethoxybenzyl,
4-Me$_2$aminobenzyl,
3-Me$_2$aminobenzyl,
4-isopropylbenzyl,
4-chlorobenzyl,
4-methoxybenzyl,
4-methylbenzyl,
3-methylbenzyl,
4-isopropoxybenzyl,
4-acetamidobenzyl,
4-methylsulfonylbenzyl,
3-methyl-4-methoxybenzyl,
3-allyloxy-4-methoxybenzyl,
3,4,5-trimethoxybenzyl,
3-n-propoxybenzyl,
4-thiomethylbenzyl,
3-carbethoxybenzyl,
3,4,5-triethoxybenzyl,
4-carbethoxybenzyl,
3-methoxybenzyl,
2-methoxybenzyl,
3-chlorobenzyl,
3,4-dimethoxy-5-(2-morpholin-4-yl-ethoxy)-benzyl,
3,4-dimethoxy-5-(3-morpholin-4-yl-propoxy)-benzyl,
3,4-dimethoxy-5-(2-dimethylaminoethoxy)-benzyl,
3,4-dimethoxy-5-(3-dimethylaminopropoxy)-benzyl,
3,4-dimethoxy-5-(2-(4-methylpiperazin)-1-yl-ethoxy)-benzyl,
3,4-dimethoxy-5-(3-(4-methylpiperazin)-1-yl-propoxy)-benzyl, or
cyclohexylmethyl;
$R_3$ is phenyl,
4-methylphenyl,
4-methoxyphenyl,

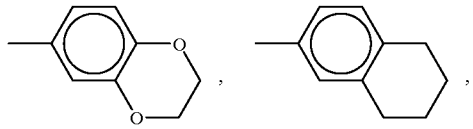

3-methoxyphenyl,
3-methyl-4-methoxyphenyl,
3,4-dimethoxyphenyl, or
2,4-dimethoxyphenyl;
$R_4$ is alkyl, unsubstituted or substituted with from 1 to 5 substituents;
aryl unsubstituted or substituted with from 1 to 5 substituents;
heteroaryl unsubstituted or substituted with from 1 to 5 substituents; and
X is oxygen.

Still more preferred compounds of the instant invention are selected from:

(1-Phenyl-ethyl)-carbamic acid-4-benzo[1,3]dioxol-5-yl-3-benzyl-2-(4-methoxy-phenyl)-5-oxo-2,5-dihydro-furan-2-yl ester, (1-Naphthalen-1-yl-ethyl)-carbamic acid-4-benzo[1,3]dioxol-5-yl-2-(4-methoxy-phenyl)-5-oxo-3-(3,4,5-trimethoxy-benzyl)-2,5-dihydro-furan-2-yl ester,

[4-Benzo[1,3]dioxol-5-yl-2-(4-methoxy-phenyl)-5-oxo-3-(3,4,5-trimethoxy-benzyl)-2,5-dihydro-furan-2-yloxycarbonylamino]-acetic acid ethyl ester, (1-Phenyl-ethyl)-carbamic acid 4-benzo[1,3]dioxol-5-yl-3-benzyl-2-(4-methoxyphenyl)-5-oxo-2,5-dihydro-furan-2-yl ester, (1-Naphthylen-1-yl-ethyl)[4-Benzo[1,3]dioxol-5-yl-2-(4-methoxyphenyl)-5-oxo-3-(3,4,5-trimethoxy-benzyl)-2,5-dihydro-furan-2-yloxycarbonylamino]-,

[4-Benzo[1,3]dioxol-5-yl-2-(4-methoxyphenyl)-5-oxo-3-(3,4,5-trimethoxy-benzyl)-2,5-dihydro-furan-2-yloxycarbonylamino]-acetic acid ethyl ester, 2-[4-Benzo[1,3]dioxol-5-yl-2-(4-methoxyphenyl)-5-oxo-3-(3,4,5-trimethoxy-benzyl)-2,5-dihydro-furan-2-yloxycarbonylamino]-3-phenyl-propionic acid ethyl ester, Methyl-carbamic acid 4-benzo[1,3]dioxol-5-yl-3-(3,4,5-trimethoxy-benzyl)-2-(4-methoxyphenyl)-5-oxo-2,5-dihydro-furan-2-yl ester, 3-[4-Benzo[1,3]dioxol-5-yl-2-(4-methoxyphenyl)-5-oxo-3-(3,4,5-trimethoxy-benzyl)-2,5-dihydro-furan-2-yloxycarbonylamino]-propionic acid ethyl ester, Allyl-carbamic acid 4-benzo[1,3]dioxol-5-yl-3-(3,4,5-trimethoxy-benzyl)-2-(4-methoxyphenyl)-5-oxo-2,5-dihydro-furan-2-yl ester, 2-[4-Benzo[1,3]dioxol-5-yl-2-(4-methoxyphenyl)-5-oxo-3-(3,4,5-trimethoxy-benzyl)-2,5-dihydro-furan-2-yloxycarbonylamino]-acetic acid, 2-[4-Benzo[1,3]dioxol-5-yl-2-(4-methoxyphenyl)-5-oxo-3-(3,4,5-trimethoxy-benzyl)-2,5-dihydro-furan-2-yloxycarbonylamino]-acetaldehyde, 2-[4-Benzo[1,3]dioxol-5-yl-2-(4-methoxyphenyl)-5-oxo-3-(3,4,5-trimethoxy-benzyl)-2,5-dihydro-furan-2-yloxycarbonylamino]-3-methyl-butryic acid ethyl ester, 3-[4-Benzo[1,3]dioxol-5-yl-2-(4-methoxyphenyl)-5-oxo-3-(3,4,5-trimethoxy-benzyl)-2,5-dihydro-furan-2-yloxycarbonylamino]-propionic acid, 2-[4-Benzo[1,3]dioxol-5-yl-2-(4-methoxyphenyl)-5-oxo-3-(3,4,5-trimethoxy-benzyl)-2,5-dihydro-furan-2-yloxycarbonylamino]-3-methyl-butryic acid, 2-[4-Benzo[1,3]dioxol-5-yl-2-(4-methoxyphenyl)-5-oxo-3-(3,4,5-trimethoxy-benzyl)-2,5-dihydro-furan-2-yloxycarbonylamino]-3-phenyl-propionic acid, 2-[4-Benzo[1,3]dioxol-5-yl-2-(4-methoxyphenyl)-5-oxo-3-(3,4,5-trimethoxy-benzyl)-2,5-dihydro-furan-2-yloxycarbonylamino]-4-methyl-pentanoic acid ethyl ester, 2-[4-Benzo[1,3]dioxol-5-yl-2-(4-methoxyphenyl)-5-oxo-3-(3,4,5-trimethoxy-benzyl)-2,5-dihydro-furan-2-yloxycarbonylamino]-4-methyl-pentanoic acid, 2-[4-Benzo[1,3]dioxol-5-yl-2-(4-methoxyphenyl)-5-oxo-3-(3,4,5-trimethoxy-benzyl)-2,5-dihydro-furan-2-yloxycarbonylamino]-4-methyl-pentanoic acid t-butyl ester, 2-[4-Benzo[1,3]dioxol-5-yl-2-(4-methoxyphenyl)-5-oxo-3-(3,4,5-trimethoxy-benzyl)-2,5-dihydro-furan-2-yloxycarbonylamino]-4-methyl-pentanoic acid benzyl ester, 2-[4-Benzo[1,3]dioxol-5-yl-2-(4-methoxyphenyl)-5-oxo-3-(3,4,5-trimethoxy-benzyl)-2,5-dihydro-furan-2-yloxycarbonylamino]-4-methyl-pentanoic acid methyl ester, 2-[4-Benzo[1,3]dioxol-5-yl-2-(4-methoxyphenyl)-5-oxo-3-(3,4,5-trimethoxy-benzyl)-2,5-dihydro-furan-2-yloxycarbonylamino]-4-methyl-pentanoic acid (2,2,2-trichlorethyl ester), 2-[4-Benzo[1,3]dioxol-5-yl-2-(4-methoxyphenyl)-5-oxo-3-(3,4,5-trimethoxy-benzyl)-2,5-dihydro-furan-2-yloxycarbonylamino]-3-carboxyethyl propionic acid-ethyl esteracetic acid, and 3-Phenyl propionic acid [4-Benzo[1,3]dioxol-5-yl-2-(4-methoxyphenyl)-5-oxo-3-(3,4,5-trimethoxy-benzyl)-2,5-dihydro-furan-2-yl] ester.

Elevated levels of endothelin have been postulated to be involved in a number of pathophysiological states including diseases associated with the cardiovascular system as well as various metabolic and endocrinological disorders. As antagonists of endothelin, the compounds of Formula I are useful in the treatment of hypertension, myocardial infarction, diabetes, cerebral vasospasm, cirrhosis, septic shock, congestive heart failure, endotoxic shock, subarachnoid hemorrhage, arrhythmias, asthma, chronic and acute renal failure, preeclampsia, atherosclerotic disorders including Raynaud's disease and restenosis, angina, cancer, pulmonary hypertension, ischemic disease, gastric mucosal damage, hemorrhagic shock, stroke, head injury, and ischemic bowel disease.

A still further embodiment of the present invention is a pharmaceutical composition for administering a therapeutically effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "alkyl" means a straight or branched hydrocarbon radical having from 1 to 12 carbon atoms unless otherwise specified and includes, for example, methyl, ethyl, n-propyl, isopropyl, n-butyl, sec-butyl, isobutyl, tert-butyl, allyl, n-pentyl, n-hexyl, n-heptyl, n-octyl, n-nonyl, n-decyl, undecyl, and dodecyl. The alkyl group is unsubstituted or substituted by from 1 to 6 substituents selected from alkyl, alkoxy, thioalkoxy all as defined herein, hydroxy, thiol, nitro, halogen, amino, mono-substituted amino, disubstituted amino, formyl, cycloalkyl, sulfonic acid,

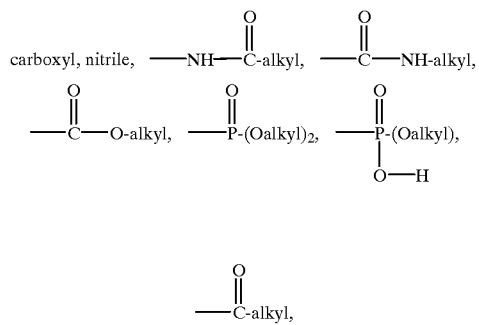

aryl, or heteroaryl wherein alkyl, aryl, and heteroaryl are defined as herein.

The term "cycloalkyl" means a saturated hydrocarbon ring which contains from 3 to 12 carbon atoms unless otherwise specified, for example, cyclopropyl, cyclobutyl, cyclopentyl, cyclohexyl, cycloheptyl, and adamantyl. The cycloalkyl ring may be unsubstituted or substituted by from 1 to 3 substituents selected from alkyl, cycloalkyl, cycloalkoxy, alkoxy, thioalkoxy all as defined herein, hydroxy, thiol, nitro, halogen, amino, monosubstituted amino, disubstituted amino, formyl, sulfonic acid, carboxyl, nitrile, alkylsulfoxyl, arylsulfoxyl, alkylsulfonyl, arylsulfonyl,

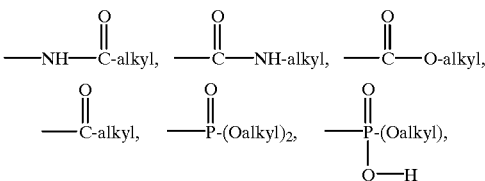

aryl, or heteroaryl wherein alkyl, aryl, and heteroaryl are defined as herein.

The terms "alkoxy" and "thioalkoxy" are O-alkyl or S-alkyl as defined above for alkyl.

Two alkoxy or thioalkoxy groups can be taken together to form a cyclic group such as

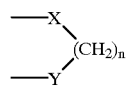

where X and Y are independently either O or S and n=1, 2, 3, or 4.

The term "aryl" means an aromatic radical which is a phenyl group, a benzyl group, a naphthyl group, a biphenyl group, a pyrenyl group, an anthracenyl group, or a fluorenyl group and the like, unsubstituted or substituted by 1 to 5 substituents selected from alkyl as defined above, alkoxy as defined above, thioalkoxy as defined above, hydroxy, thiol, nitro, halogen, sulfonic acid, amino, monosubstituted amino, disubstituted amino, formyl, carboxy, nitrile, arylsulfoxyl, alkylsulfoxyl, arylsulfonyl, alkylsulfonyl,

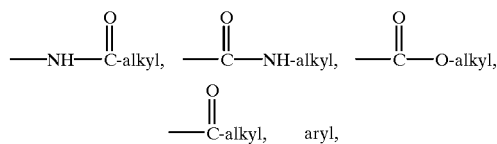

or heteroaryl wherein alkyl, aryl, and heteroaryl are defined as above.

The term "heteroaryl" means a heteroaromatic radical which is 2-or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, or 2-, 4-, 5-, 6-, or 7-benzoxazolyl, 2-, 4-, 5-, 6-, or 7-benzimidazolyl, 2-, 4-, 5-, 6-, or 7-benzothiazolyl, unsubstituted or substituted by 1 to 3 substituents selected from alkyl as defined above, aryl as defined above, alkoxy as defined above, thioalkoxy as defined above, hydroxy, thiol, nitro, halogen, formyl, amino, monosubstituted amino, disubstituted amino, carboxyl, sulfonic acid,

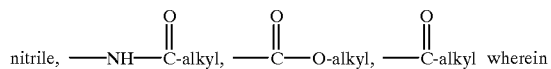

alkyl is as defined above or phenyl.

"Halogen" is fluorine, chlorine, bromine or iodine.

Some of the compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, isethionic and the like. Also contemplated are salts of amino acids such as lysinate, arginate, and the like and gluconate, galacturonate (see, for example, Berge S. M., et al., "Pharmaceutical Salts," *Journal of Pharmaceutical Science*, 1977;66:1–19).

The acid addition salts of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, piperazine, dicyclohexylamine, ethylenediamine, N-methylglucamine, and procaine (see, for example, Berge S. M., et al., "Pharmaceutical Salts," *Journal of Pharmaceutical Science*, 1977;66:1–19).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

The compounds of the present invention possess one or more chiral centers and each center may exist in the R(D) or S(L) configuration. The present invention includes all enantiomeric and epimeric forms as well as the appropriate mixtures thereof.

The compounds of Formula I are valuable antagonists of endothelin. The tests employed indicate that compounds of the invention possess endothelin antagonist activity. Thus, the compounds were tested for their ability to inhibit [$^{125}$I]-ET-1([$^{125}$I]-Endothelin-1) binding in a receptor assay. Selected compounds were also tested for antagonist activity by inhibition of ET-1 stimulated arachidonic acid release and ET-1 stimulated vasoconstriction. The following testing procedures were used (Doherty A. M., et al., "Design of C-Terminal Peptide Antagonists of Endothelin: Structure-Activity Relationships of ET-1 [16-21, D-His$^{16}$]", *Bioorganic and Medicinal Chemistry Letters*, 1993;3:497–502).

ENDOTHELIN RECEPTOR BINDING ASSAY-A (ERBA-A) INTACT CELL BINDING OF [$^{125}$I]-ET-1

Materials and Terms Used:

Cells

The cells used were rabbit renal artery vascular smooth muscle cells grown in a 48-well dish (1 cm$^2$) (confluent cells).

Growth Media

The growth media was Dulbecco's Modified Eagles/Ham's F12 which contained 10% fetal bovine serum and antibiotics (penicillin/streptomycin/fungizone).

Assay Buffer

The assay buffer was a medium 199 containing Hanks salts and 25 mM Hepes buffer (Gibco 380-2350AJ), supplemented with penicillin/streptomycin/fungizone (0.5%) and bovine serum albumin (1 mg/mL).

[$^{125}$I]-ET-1

Amersham radioiodinated endothelin-1 [$^{125}$I]-ET-1 was used at final concentration of 20,000 cpm/0.25 mL (25 pM).

Protocol

First, add 0.5 mL warm assay buffer (described above) to the aspirated growth media and preincubate for 2 to 3 hours in a 37° C. water bath (do not put back in the 5% carbon dioxide). Second, remove the assay buffers, place the dish on ice, and add 150 μL of cold assay buffer described above to each well. Third, add 50 mL each of cold [$^{125}$I]-ET-1 and competing ligand to the solution (at the same time if possible). Next, place dish in a 37° C. water bath for about 2 hours and gently agitate the dish every 15 minutes. Discard the radioactive incubation mixture in the sink and wash wells 3 times with 1 mL of cold phosphate buffered saline. Last, add 250 mL of 0.25 molar sodium hydroxide, agitate for 1 hour on a rotator, and then transfer the sodium hydroxide extract to gamma counting tubes and count the radioactivity.

ENDOTHELIN RECEPTOR BINDING ASSAY-B (ERBA-B) [$^{125}$I]-ET-1 BINDING IN RAT CEREBELLAR MEMBRANES

Materials and Terms 2sed:

Tissue Buffer

The tissue is made up of 20 mM tris(hydroxy-methyl) aminomethane hydrochloride (Trizma) buffer, 2 mM ethylenediaminetetra acetate, 100 μM phenylmethyl-sulfonyl fluoride.

Tissue Preparation

First, thaw one aliquot of frozen rat cerebellar membranes (2 mg protein in 0.5 mL). Next, add 0.5 mL membrane aliquot to 4.5 mL cold tissue buffer, polytron at 7,500 revolutions per minute for 10 seconds. Finally, dilute tissue suspension 1/100 (0.1 mL suspension+9.9 mL tissue buffer), polytron again, and place ice.

Dilution Buffer

Medium 199 with Hank's salts plus 25 mM Hepes+1 mg/mL bovine serum albumin.

[$^{125}$I]-ET-1

Amersham [$^{125}$I]-ET-1 (aliquots of 2×10$^6$ cpm per 100-mL aliquot of [$^{125}$I]-ET-1 with 5.2 mL dilution buffer, place on ice until use (final concentration will be 20,000 cpm per tube, or 25 pM).

Protocol

Add 50 μL each of cold [$^{125}$]-ET-1 and competing ligand to tubes on ice. Mix in 150 μL of tissue to each tube, vortex briefly, then tap to force all liquids to bottom (total assay volume=250 μL). Then place the tubes in a 37° C. water bath for 2 hours.

Add 2.5 mL cold wash buffer (50 mM Trizma buffer) to each tube, filter, and then wash tube with additional 2.5 mL wash buffer and add to filter. Finally, wash filters with an additional 2.5 mL of cold wash buffer.

Count filters for radioactivity in gamma counter.

The above process has also been modified by using human recombinant CHO-K1 cells.

The tissue used for human ETB was recombinant human ETB receptor expressed in CHO-K1 cells (chinese hamster ovary cells). The gene for human ETB receptor was cloned and inserted into the pRc-CMW expression vector, then transfected into CHO-K1 cells by electroporation. For binding assays, membranes (0.7 mg protein) of CHO-K1 cells expressing recombinant human ETB receptor were used.

IN VITRO INHIBITION OF ET-1 STIMULATED ARACHIDONIC ACID RELEASE (AAR) IN CULTURED RABBIT VASCULAR SMOOTH MUSCLE CELLS (ET$_A$) BY THE COMPOUNDS OF THE INVENTION

Antagonist activity is measured by the ability of added compounds to reduce endothelin-stimulated arachidonic acid release in cultured vascular smooth muscle cells as arachidonic acid release (AAR). [$^3$H] Arachidonic Acid Loading Media (LM) is DME/F12+0.5% FCS×0.25 mCi/mL [$^3$H] arachidonic acid (Amersham). Confluent monolayers of cultured rabbit renal artery vascular smooth muscle cells were incubated in 0.5 mL of the LM over 18 hours, at 37° C., in 5% CO$_2$. The LM was aspirated and the cells were washed once with the assay buffer (Hank's BSS+10 mM HEPES+fatty acid-free BSA (1 mg/mL)), and incubated for 5 minutes with 1 mL of the prewarmed assay buffer. This solution was aspirated, followed by an additional 1 mL of prewarmed assay buffer, and further incubated for another 5 minutes. A final 5-minute incubation was carried out in a similar manner. The same procedure was repeated with the inclusion of 10 μL of the test compound (1 nM to 1 μM) and 10 μL ET-1 (0.3 nM) and the incubation was extended for 30 minutes. This solution was then collected, 10 μL of scintillation cocktail was added, and the amount of [$^3$H] arachidonic acid was determined in a liquid scintillation counter.

IN VITRO ANTAGONISM OF ET-1 STIMULATED VASOCONSTRICTION (VERA-A) IN THE RABBIT FEMORAL ARTERY (ET$_A$) AND SARAFOTOXIN 6c STIMULATED VASOCONSTRICTION IN THE RABBIT PULMONARY ARTERY (ET$_B$)

Male New Zealand rabbits were killed by cervical dislocation and exsanguination. Femoral and pulmonary arteries were isolated, cleaned of connective tissue, and cut into 4-mm rings. The endothelium was denuded by placing the rings over hypodermic tubing (32 gauge for femoral rings and 28 gauge for pulmonary rings, Small Parts, Inc, Miami, Fla.) and gently rolling them. Denuded rings were mounted in 20 mL organ baths containing Krebs-bicarbonate buffer (composition in mM: NaCl, 118.2; NaHCO$_3$, 24.8; KCl, 4.6; MgSO$_4$ 7. H$_2$O, 1.2; KH$_2$PO$_4$, 1.2; CaCl$_2$. 2H$_2$O; Ca-Na$_2$ EDTA, 0.026; dextrose, 10.0), that was maintained at 37° C. and gassed continuously with 5% CO$_2$ in oxygen (pH 7.4). Resting tension was adjusted to 3.0 g for femoral and 4.0 g pulmonary arteries; the rings were left for 90 minutes to equilibrate. Vascular rings were tested for lack of functional endothelium (i.e., lack of an endothelium-dependent relaxation response to carbachol (1.0 μM) in norepinephrine (0.03 μM) contracted rings. Agonist peptides, ET-1 (femoral), and S6c (pulmonary), were cumulatively added at 10- minute intervals. The ET antagonists were added 30 minutes prior to adding the agonist and pA$_2$ values were calculated (Table II).

The data in Table II below show the endothelin receptor binding and antagonist activity of representative compounds of the instant invention.

TABLE II

| Example | ERBA-A[a] | ERBA-B[a] | AAR-A[c] | VERA-A[b] |
| --- | --- | --- | --- | --- |
| 1 | 18.0[c] | >2500[c] | — | 6.1 |
| 2 | 1.0[c] | >2500[c] | — | — |
| 3 | 0.35[c] | 1800[c] | 3.4 | 7.3 |

[a]IC$_{50}$ values in nM
[b]pA2 values
[c]Human cloned receptor data

As can be seen in Table II above, the compounds of Formula I bind to the endothelin receptors ET$_A$ (ERBA-A) and ET$_B$ (ERBA-B) in the μM to nM range.

The said compounds also reduce endothelin-stimulated arachidonic acid release (AAR) and therefore are functional antagonists.

Furthermore, in vitro activity is demonstrated by the antagonism of endothelin-stimulated vasoconstriction of rabbit femoral artery.

GENERAL SYNTHETIC APPROACHES

The compounds of Formula I may be prepared as in Scheme I.

Condensation of the alcohol of the generic α-hydroxybutenolide with an isocyanate in a nonprotic solvent (such as methylenechloride, acetonitrile, ethylacetate) with or without a catalyst (such as DMAP, $CuCl_2$).

SCHEME I

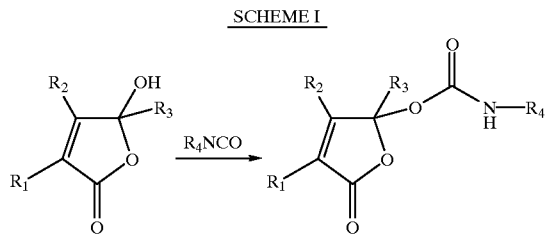

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions and/or any of the additions generally regarded as safe. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antagonists of endothelin, the compounds utilized in the pharmaceutical method of this invention are administered at the initial dosage of about 0.01 mg to about 100 mg/kg daily. A daily dose range of about 0.01 mg to about 10 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

EXAMPLE 1

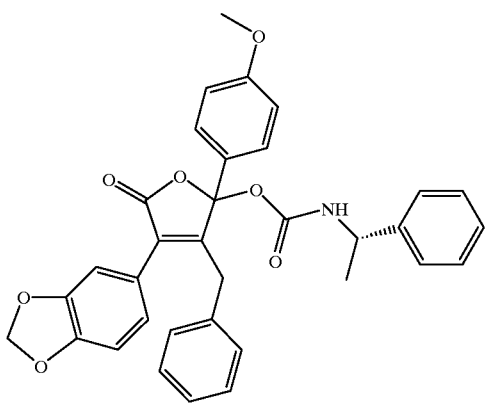

(1-Phenyl-ethyl)-carbamic acid-4-benzo[1,3]dioxol-5-yl-3-benzyl-2-(4-methoxy-phenyl)-5-oxo-2,5-dihydro-furan-2-yl ester To 15 mL dichloromethane was added 3-benzo[1,3]dioxol-5-yl-5-hydroxy-5-(4-methoxyphenyl)-4-(benzyl)-5H-furan-2-one 416 mg (1.00 mmol) and stirred to dissolve. To this was added (S)-1-(1-phenyl)ethyl isocyanate 162 mg (1.1 mmol), and the mixture was stirred at room temperature for 24 hours. To the mixture was added a catalytic amount of 4-dimethylaminopyridine 15 mg (0.123 mmol). The mixture was stirred at room temperature for 24 hours. The solution was washed with 25 mL water and 25 mL brine, and the organic phase was separated and dried over magnesium sulfate, then evaporated to dryness. The crude product was then purified by flash chromatography (70 g silica gel, 33% EtOAc/Hexane). The product was isolated by evaporation of the appropriate fractions to give 310 mg (55%) as a white foam. The product was identified by $^1$H NMR, IR, MS, $[M+H]^+$=546 Da. and microanalysis.

EXAMPLE 2

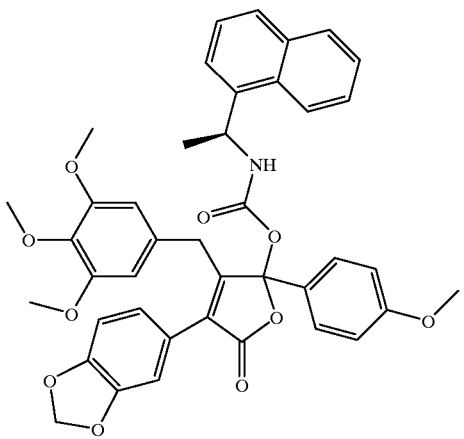

(1-Naphthalen-1-yl-ethyl)-carbamic acid-4-benzo [1,3]dioxol-5-yl-2-(4-methoxy-phenyl)-5-oxo-3-(3,4,5-trimethoxy-benzyl)-2,5-dihydro-furan-2-yl ester To 15 mL dichloromethane was added 3-benzo[1,3]dioxol-5-yl-5-hydroxy-5-(4-methoxyphenyl)-4-(3,4,5-trimethoxy-benzyl)-5H-furan-2-one 1.00 g (1.98 mmol) and stirred to dissolve. To this was added (S)-1-(1-naphthyl) ethyl isocyanate 414 mg (2.1 mmol) and a catalytic amount of 4-dimethylaminopyridine 20 mg (0.164 mmol). The mixture was stirred at room temperature for 24 hours. The solution was washed with 50 mL water and 50 mL brine, and the organic phase was separated and dried over magnesium sulfate, then evaporated to dryness. The crude product was then purified by flash chromatography (150 g silica gel, 10% EtOAc/CH$_2$Cl$_2$). The product was isolated by evaporation of the appropriate fractions to give 840 mg (60%) as a white foam. The product was identified by $^1$H NMR, MS, $[M+H]^+$=704 Da. and microanalysis.

EXAMPLE 3

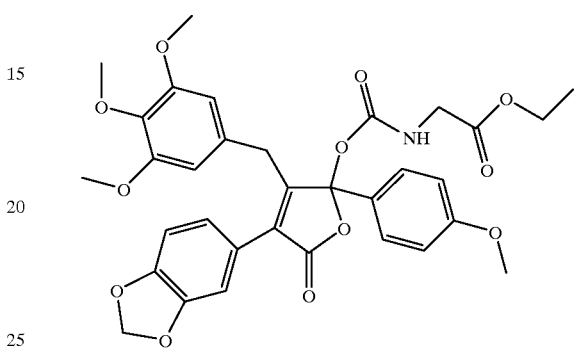

[4-Benzo[1,3]dioxol-5-yl-2-(4-methoxy-phenyl)-5-oxo-3-(3,4,5-trimethoxy-benzyl)-2,5-dihydro-furan-2-yloxycarbonylaminol-acetic acid ethyl ester To 15 mL dichloromethane was added 3-benzo[1,3]dioxol-5-yl-5-hydroxy-5-(4-methoxyphenyl)-4-(3,4,5-trimethoxybenzyl)-5H-furan-2-one 1.00 g (1.97 mmol) and stirred to dissolve. To this was added ethyl isocyanato acetate 284 mg (2.2 mmol) and a catalytic amount of 4-dimethylaminopyridine 10 mg (0.082 mmol). The mixture was stirred at room temperature for 24 hours. The solution was washed with 25 mL 1.0N HCl, 25 mL water, and 25 mL brine, and the organic phase was separated and dried over magnesium sulfate, then evaporated to dryness. The crude product was then purified by flash chromatography (150 g silica gel, 10% EtOAc/CH$_2$C$_{12}$). The product was isolated by evaporation of the appropriate fractions to give 122 mg (9.7%) as a white foam. The product was identified by $^1$H NMR, MS, $[M+H]^+$=636 Da. and microanalysis.

We claim:

1. A method of treating congestive heart failure and myocardial infarction/myocardial ischemia comprising administering to a host suffering therefrom a therapeutically effective amount of a compound of formula I

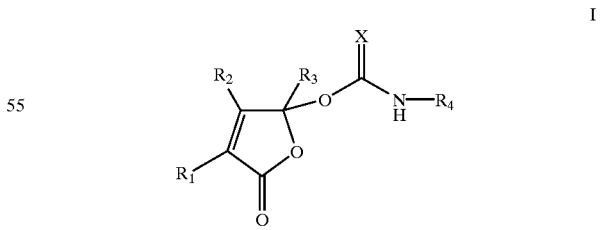

I or a pharmaceutically acceptable salt thereof wherein:
  $R_1$ is cycloalkyl substituted or unsubstituted of from 3 to 12 carbon atoms,
  phenyl substituted with from 1 to 5 substituents,
  naphthyl unsubstituted or substituted with from 1 to 5 substituents, or heteroaryl unsubstituted or substituted with from 1 to 5 substituents which heteroaryl has only oxygen as the heteroatom;

R$_2$ is alkyl substituted or unsubstituted straight, or branched, of from 1 to 12 carbon atoms, cycloalkyl substituted or unsubstituted of from 3 to 12 carbon atoms, aryl which is unsubstituted or substituted with from 1 to 5 substituents, heteroaryl which is unsubstituted or substituted with from 1to 5 substituents which heteroaryl has only oxygen as the heteroatom;

R$_3$ is alkyl substituted or unsubstituted straight, or branched, of from 1 to 12 carbon atoms, cycloalkyl substituted or unsubstituted of from 3 to 12 carbon atoms, aryl which is unsubstituted or substituted with from 1 to 5 substituents, heteroaryl which is unsubstituted or substituted with from 1 to 5 substituents which heteroaryl has only oxygen as the heteroatom;

R4 is alkyl, unsubstituted or substituted with from 1 to 5 substituents;

aryl unsubstituted or substituted with from 1 to 5 substituents;

heteroaryl unsubstituted or substituted with from 1 to 5 substituents which heteroaryl has only oxygen as the heteroatom; and X is O or S with the proviso that (1-phenyl-ethyl)-carbamic acid-4-benzo[1,3]dioxol-5-yl-3-benzyl-2-(4-methoxy-phenyl)-5-oxo-2,5-dihydro-furan-2-yl ester is not included and furthermore, at least one of R1–R4 group represents a heteroaryl group in unit dosage form.

2. A method of treating subarachnoid hemorrhage, cerebral ischemia and/or cerebral infarction; or ischemic disease comprising administering to a host suffering therefrom a therapeutically effective amount of a compound of formula I

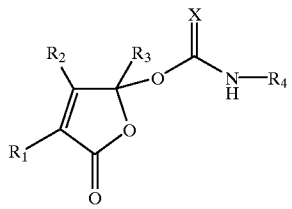

I or a pharmaceutically acceptable salt thereof wherein:

R$_1$ is cycloalkyl substituted or unsubstituted of from 3 to 12 carbon atoms, phenyl substituted with from 1 to 5 substituents, naphthyl unsubstituted or substituted with from 1 to 5 substituents, or heteroaryl unsubstituted or substituted with from 1 to 5 substituents which heteroaryl has only oxygen as the heteroatom;

R$_2$ is alkyl substituted or unsubstituted straight, or branched, of from 1 to 12 carbon atoms, cycloalkyl substituted or unsubstituted of from 3 to 12 carbon atoms, aryl which is unsubstituted or substituted with from 1 to 5 substituents, heteroaryl which is unsubstituted or substituted with from 1 to 5 substituents which heteroaryl has only oxygen as the heteroatom;

R$_3$ is alkyl substituted or unsubstituted straight, or branched, of from 1 to 12 carbon atoms, cycloalkyl substituted or unsubstituted of from 3 to 12 carbon atoms, aryl which is unsubstituted or substituted with from 1 to 5 substituents, heteroaryl which is unsubstituted or substituted with from 1 to 5 substituents which heteroaryl has only oxygen as the heteroatom;

R4 is alkyl, unsubstituted or substituted with from 1 to 5 substituents;

aryl unsubstituted or substituted with from 1 to 5 substituents;

heteroaryl unsubstituted or substituted with from 1 to 5 substituents which heteroaryl has only oxygen as the heteroatom; and X is O or S with the proviso that (1-phenyl-ethyl)-carbamic acid-4benzo[1,3]dioxol-5-yl-3-benzyl-2-(4-methoxy-phenyl)-5-oxo-2,5-dihydro-furan-2-yl ester is not included and furthermore, at least one of R1–R4 group represents a heteroaryl group in unit dosage form.

* * * * *